(12) United States Patent
Bazar et al.

(10) Patent No.: US 10,250,403 B2
(45) Date of Patent: Apr. 2, 2019

(54) DYNAMIC CONTROL OF SMART HOME USING WEARABLE DEVICE

(71) Applicant: ECOBEE INC., Toronto (CA)

(72) Inventors: Sandeep Bazar, Warangal (IN);
Kaustubh I. Katruwar, Pune (IN);
Sandeep R. Patil, Pune (IN); Sachin C. Punadikar, Pune (IN)

(73) Assignee: International Business Machines Corporation, Armonk, NY (US)

( * ) Notice: Subject to any disclaimer, the term of this patent is extended or adjusted under 35 U.S.C. 154(b) by 469 days.

(21) Appl. No.: 14/948,674

(22) Filed: Nov. 23, 2015

(65) Prior Publication Data

US 2017/0149580 A1    May 25, 2017

(51) Int. Cl.
*H04L 12/28* (2006.01)
*G05B 15/02* (2006.01)
(Continued)

(52) U.S. Cl.
CPC .......... *H04L 12/2816* (2013.01); *F24F 11/30* (2018.01); *G05B 15/02* (2013.01);
(Continued)

(58) Field of Classification Search
CPC ... H04L 12/2816; G05B 15/02; Y10S 128/92; F24F 11/66; F24F 2120/00–2120/20;
(Continued)

(56) References Cited

U.S. PATENT DOCUMENTS

| 5,515,858 A | 5/1996 | Myllymaki |
|---|---|---|
| 6,348,867 B1 | 2/2002 | Myllymaki |

(Continued)

FOREIGN PATENT DOCUMENTS

| CN | 103728953 A | 4/2014 |
|---|---|---|
| CN | 103777615 A | 5/2014 |

(Continued)

OTHER PUBLICATIONS

U.S. Appl. No. 15/018,943, filed Feb. 9, 2016, Entitled "Dynamic Control of Smart Home Using Wearable Device".
(Continued)

*Primary Examiner* — David Lam
(74) *Attorney, Agent, or Firm* — Walter L. Rudberg; Brian M. Restauro

(57) ABSTRACT

Embodiments of the present invention provide a method and system for dynamically controlling an appliance based on information received from a wearable device, to regulate the user's health. A wearable device is identified and configured to monitor at least one physiological aspect of the user. A controllable appliance with at least one sensor and at least one controllable setting is also identified. Health information of the user is received and utilized in generating, a user profile which comprises parameters related to the health of the user. Data from the wearable device and data from the controllable appliance is analyzed and it is determined whether the data matches the parameters related to the health of the user. If the data does not match the parameters related to the health of the user, then at least one controllable setting of the at least one controllable appliance is adjusted.

17 Claims, 4 Drawing Sheets

(51) Int. Cl.
  *F24F 11/30* (2018.01)
  *G06F 1/16* (2006.01)
  *F24F 120/20* (2018.01)
  *F24F 120/10* (2018.01)
  *F24F 120/12* (2018.01)
  *F24F 110/10* (2018.01)

(52) U.S. Cl.
  CPC .......... *G06F 1/163* (2013.01); *H04L 12/2803* (2013.01); *H04L 12/2829* (2013.01); *F24F 2110/10* (2018.01); *F24F 2120/10* (2018.01); *F24F 2120/12* (2018.01); *F24F 2120/20* (2018.01)

(58) Field of Classification Search
  CPC .... Y02B 70/32–70/3275; Y04S 20/24–20/244
  See application file for complete search history.

(56) References Cited

U.S. PATENT DOCUMENTS

| | | | |
|---|---|---|---|
| 7,423,526 | B2 | 9/2008 | Despotis |
| 7,598,878 | B2 | 10/2009 | Goldreich |
| 8,500,604 | B2 | 8/2013 | Srinivasan et al. |
| 8,894,576 | B2 | 11/2014 | Alwan et al. |
| 2003/0181795 | A1* | 9/2003 | Suzuki ................ A61B 5/0002 600/300 |
| 2012/0330387 | A1 | 12/2012 | Ferraz Rigo et al. |
| 2013/0204408 | A1 | 8/2013 | Thiruvengada et al. |
| 2014/0244001 | A1 | 8/2014 | Glickfield et al. |
| 2015/0164376 | A1* | 6/2015 | Huang ................ A61B 5/6801 600/302 |
| 2015/0223705 | A1 | 8/2015 | Sadhu |
| 2015/0331396 | A1 | 11/2015 | Sami |
| 2016/0061472 | A1 | 3/2016 | Lee et al. |
| 2016/0150350 | A1 | 5/2016 | Ingale et al. |
| 2016/0287142 | A1 | 10/2016 | Han et al. |
| 2017/0124276 | A1 | 5/2017 | Tee |
| 2017/0212485 | A1 | 7/2017 | Lee et al. |
| 2017/0370604 | A1 | 12/2017 | Carey et al. |

FOREIGN PATENT DOCUMENTS

| | | |
|---|---|---|
| CN | 104197470 A | 12/2014 |
| CN | 204358910 U | 5/2015 |

OTHER PUBLICATIONS

List of IBM Patents or Patent Applications Treated as Related, Dated Feb. 9, 2016, 2 pages.

Bazar et al. "Dynamic Control of Smart Home Using Wearable Device", U.S. Appl. No. 15/675,819, filed Aug. 14, 2017, 22 pages.

Appendix P—List of IBM Patents or Patent Applications Treated as Related, Filed herewith, 2 Pages.

England, "Google's newest patent tells you which method of travel will help you stay fit, and still make it to work on time", Business Insider, Jun. 9, 2015, 6 pages, <www.businessinsider.in/Googles-newest-patent-tells-you-which-method-of-travel-will-help-you-stay-fit-and-still-make-it-to-work-on-time/articleshow/47602129.cms>.

Kannan, "Sudden change from hot to cold can harm health", The National, Aug. 25, 2012, 6 pages, <http://www.thenational.ae/news/uae-news/environment/sudden-change-from-hot-to-cold-can-harm-health>.

"Meet the Nest Thermostat", Nest, Printed Aug. 19, 2015, 5 pages, <https://nest.com/thermostat/meet-nest-thermostat/>.

Bazar et al., U.S. Appl. No. 15/233,366, filed Aug. 10, 2016, Entitled "Dynamic Control of Smart Home Using Wearable Device".

List of IBM Patents or Patent Applications Treated as Related, Dated Aug. 10, 2016, 2 pages.

* cited by examiner

DYNAMIC CONTROL OF SMART HOME USING WEARABLE DEVICE

BACKGROUND OF THE INVENTION

The present invention relates generally to the field of controlling a home automation system and, in particular, to controlling a home automation system by a wearable device, to regulate the user's health.

Advances in electronic technology allow for near instantaneous communication and data exchange, while leading to ever smaller devices. Recent advances in sensor technology, as well as the miniaturization of both electronics and power sources allow for the scaling down of commonly used devices. Specifically, computing devices have benefited from recent advancements in microprocessor design, providing increasingly complex computations while providing successively diminutive size.

Many smart devices provide a user with access to computing capabilities even as the user moves about to various locations. Wearable technological computing devices include non-intrusive devices a user may wear on their body without impeding daily activities. Common wearable devices may include a watch, ring, necklace, bracelet or other wrist worn device. Such devices may work independently, connect to a network, or sync to another electronic device such as a smart device similar to a mobile phone. Many wearable electronic devices include 'smartness' features which enables them to be programmed to operate in different modes. Such devices may have the ability to be programmed for a fixed routine and can work (start/stop/other operations) accordingly. Alternatively such devices may even be started on an occurrence of a particular event as well.

SUMMARY

According to one embodiment of the present invention, a method for controlling an appliance based on a physiological aspects of a user is provided, the method comprising: identifying, by one or more processors, a wearable device, with at least one user sensor, wherein the wearable device is associated with a user, and wherein the at least one user sensor monitors at least one physiological aspect of the user; identifying, by one or more processors, at least one controllable appliance associated with the user, with at least one appliance sensor and at least one controllable setting; receiving, by one or more processors, health information of the user; in response to receiving the health information of the user, generating, by one or more processors, a user profile, wherein the user profile comprises parameters related to the health of the user; receiving, by one or more processors, a first set of data from the wearable device and a second set of data from the at least one controllable appliance; determining, by one or more processors, whether the received first set of data and the received second set of data matches the parameters related to the health of the user; and in response to determining that the received data does not match the parameters related to the health of the user, adjusting, by one or more processors, at least one controllable setting of the at least one controllable appliance, so that the second set of data from the at least one controllable appliance and the first set of data from the wearable device matches the user profile.

Another embodiment of the present invention provides a computer program product for controlling an appliance based on a physiological aspects of a user, based on the method described above.

Another embodiment of the present invention provides a computer system for controlling an appliance based on a physiological aspects of a user, based on the method described above.

DETAILED DESCRIPTION

Figure 1:
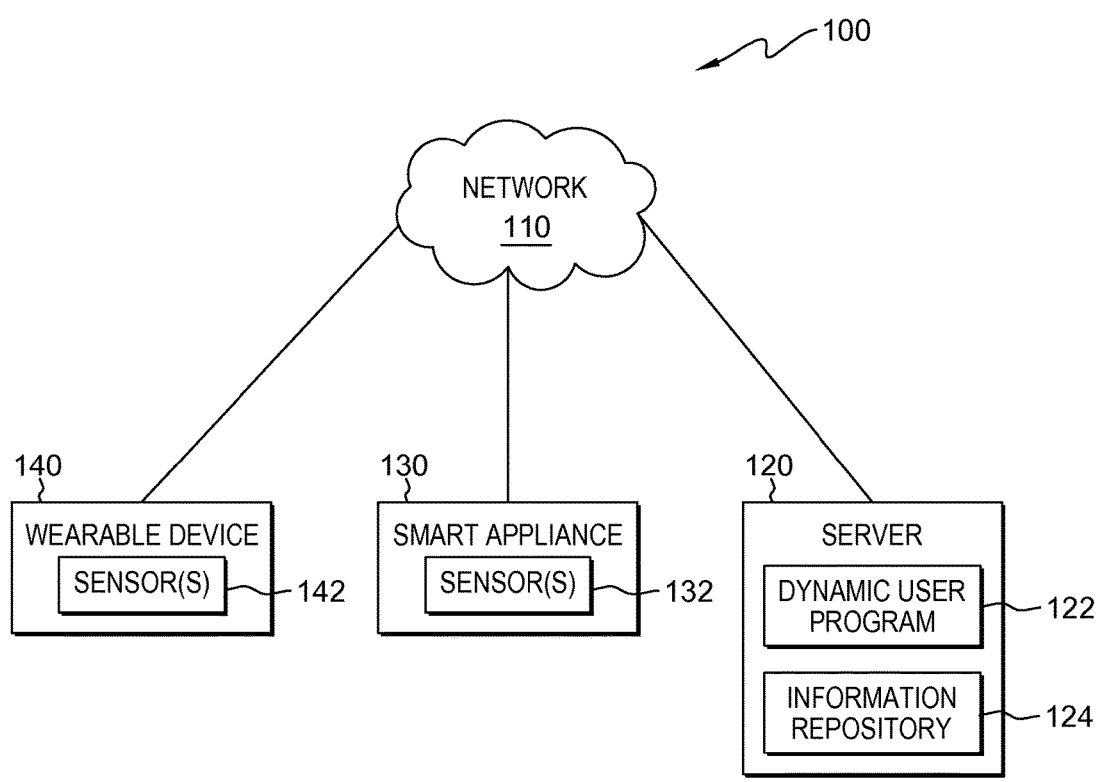
FIG. 1 is a functional block diagram illustrating a data processing environment, in accordance with an embodiment of the present invention.

Electronic devices have become an essential part of daily life. The small size of computing devices allows them to be easily portable and even wearable. Wearable devices, are unobtrusive for the wearer, as they are small and light weight.

Advances in electronic technology allow for devices to communicate and exchange data. Many devices have 'smartness' features enabling such devices to be programmed to operate in different modes. For example, devices may be programmed for a fixed routine providing various operations (i.e., start, stop, etc.). For instance, at a predetermined time, powering on an air conditioner and/or heater, to make the environment comfortable when the user arrives. Similarly, in another instance, at a predetermined time, powering on an oven (with food already in it), such that a meal will be ready when the user returns home from a day at work. Such devices may even be started on an occurrence of a particular event. For instance, a water pump may engage and fill a water tank on sensing a low water level.

With wide spread of the Internet of things (IOT), there is an emergence of new abilities to control consumer devices using applications that are installed on smart devices (referred to hereinafter as 'App'). The IOT is the network of physical objects (devices) containing electronic sensors, software and network connectivity, which enable the physical objects to collect and exchange data with other physical devices and/or electronic systems. The IOT, through a network infrastructure, allows objects to be sensed and controlled remotely, integrating physical objects with electronic computer systems.

In an exemplary embodiment of the present invention, IOT may be used to monitor and control various mechanical and electrical systems used in one's home. For example, IOT may be used to improve a person's personal comfort, convenience, and security by controlling lighting, heating, ventilation, air conditioning, appliances, communication systems, and home security systems. For instance, utilizing a device's tracking information, such as location of a user, an App may help automatically activate one or more consumer devices at home on meeting pre-determined criteria.

Embodiments of the present invention provide systems and methods to automatically utilize a wearable device by receiving and analyzing inputs for various user parameters activities, and then accordingly controls/programs the IOT enabled appliances used by the user to ensure that the health profile of the user is maintained. Additionally, embodiments of the present invention provide systems and methods to automatically control the IOT if the user's normal routine is altered in order to improve the user's personal comfort, and/or physiological health.

Embodiments of the present invention derive different user activities that directly and/or indirectly relate with the health of the user, and through IOT influence the functioning of smart appliances to benefit the user's health. The user's health may be determined from the body temperature of the user.

It is to be understood that while the concepts included herein are presented in the context of a wearable device, the concepts disclosed herein may be applied in other contexts as well if the appropriate hardware is available.

The present invention will now be described in detail with reference to the Figures. FIG. 1 is a functional block diagram illustrating a data processing environment, in accordance with an embodiment of the present invention. FIG. 1 provides only an illustration of one embodiment and does not imply any limitations with regard to the environments in which different embodiments may be implemented. Many modifications to the depicted environment may be made by those skilled in the art without departing from the scope of the invention, as recited by the claims.

In the depicted embodiment, environment 100 includes server 120, smart appliance 130, wearable device 140, all interconnected over network 110. Server 120, smart appliance 130 and wearable device 140 may include internal and external hardware components, as depicted and described in further detail with respect to FIG. 4.

Network 110 may be a local area network (LAN), a wide area network (WAN), such as the Internet, the public switched telephone network (PSTN), a mobile data network (e.g., wireless Internet provided by a third or fourth generation of mobile phone mobile communication), a private branch exchange (PBX), any combination thereof, or any combination of connections and protocols that will support communications between server 120, smart appliance 130, and wearable device 140, in accordance with embodiments of the invention. Network 110 may include wired, wireless or fiber optic connections. Environment 100 may include additional computing devices, servers or other devices not shown.

In the exemplary embodiment, server 120 is a server computer. In other embodiments, server 120 may be a management server, a web server or any other electronic device capable of receiving and sending data. In another embodiment, server 120 may represent a server computing system utilizing multiple computers as a server system, such as in a cloud computing environment. Server 120 contains dynamic user program 122, and information repository 124.

In the various embodiments of the present invention, dynamic user program 122 receives various data, for example geographical and physiological of a user, and determines how to improve the user's personal comfort, and/or physiological health corresponding to the detected received data.

Dynamic user program 122 may track geological locations and physiological conditions of the user via sensor(s) 142 in wearable device 140. Dynamic user program 122 operates generally to control smart appliance 130 based on a user's geological location and physiological condition. Dynamic user program 122 analyzes all information contained in information repository 124 relating to a specific user's wearable device 140. While depicted on server 120, in the exemplary embodiment, dynamic user program 122 may be located on wearable device 140, maintaining and managing smart appliances 130.

In an embodiment dynamic user program 122 receives various data, for example geographical and physiological of a user. Dynamic user program 122 may analyze data received from sensor(s) 132 and sensor(s) 142.

Dynamic user program 122 may analyze data received from additional sensor(s) not show in environment 100. Dynamic user program 122, may for example intelligently track numerous aspects of a user based on information received from sensor(s) 142. Utilizing at least one sensor(s) 142, the wearable program may detect various geographical and physiological aspects of a user, which correlate to specific predetermined activity.

For example, dynamic user program 122 may detect a routinely occurring activity pattern for a specific day, date and/or time. Thereby if the user breaks from his regular routine, dynamic user program 122 will automatically adjust smart appliance 130 accordingly.

In another example, dynamic user program 122 may detect a spike in a user's physiological condition, and automatically adjust smart appliance 130 to assist the user accordingly. For example, if a user's heartrate and temperate rise, dynamic user program 122 may determine a user is working out and automatically adjust the thermostat at the user's house to best suit the user. In another example, sensors determine that the user is sleeping, dynamic user program 122 may derive a specific meal to eat when the user wakes up conforming to the user's health profile as provided by a dietitian.

Dynamic user program 122 may include a user interface allowing a user to interact with the program and set baseline parameters. The user interface may be a graphical user interface. For example, the graphical user interface may include a dashboard to view a listing of all registered smart appliances, ability to remove a smart appliance, ability to add a new smart appliance as well as details of the user's physiological parameters.

Information repository 124 may include any suitable volatile or non-volatile computer readable storage media, and may include random access memory (RAM) and cache memory (not depicted in FIG. 1). Dynamic user program 122 may be stored in a persistent storage component (not depicted) for execution and/or access by one or more of processor(s) via one or more memories (for more detail refer to FIG. 4). Alternatively, or in addition to a magnetic hard disk drive, the persistent storage component can include a solid state hard drive, a semiconductor storage device, read-only memory (ROM), erasable programmable read-only memory (EPROM), flash memory, or any other computer readable storage media that is capable of storing program instructions or digital information.

Information repository 124 can be implemented using any architecture known in the art such as, for example, a relational database, an object-oriented database, and/or one or more tables. Information repository 124 stores actual, modeled, predicted, or otherwise derived patterns of movement based on sensor data. For example, information repository 124 stores all information received from wearable device 140. Information repository 124 may contain lookup tables, databases, charts, graphs, functions, equations, and the like that dynamic user program 122 may access to both maintain a specific parameter as well as manipulate various parameters on smart appliance 130. Information stored in information repository 124 may include: various geographical locations, specific physiological actions linked to the various geographical locations, various user patterns, and the like. While depicted on server 120, in the exemplary embodiment, information repository 124 may be on a remote server or a "cloud" of computers interconnected by one or more networks utilizing clustered computers and components to act as a single pool of seamless resources, accessible to dynamic user program 122 via network 110.

In the various embodiments of the present invention, smart appliance 130 represents any physical object of the IOT which may be controlled to affect the physiological wellbeing of a user, and/or to increase the overall environment efficiency by minimizing wasted electricity. It is noted that although FIG. 1 depicts only one smart appliance 130, there can be numerous smart appliances receiving commands from dynamic user program 122. For example, smart appliance 130 many include a user's oven, car, smart phone, smart TV, heating air conditioning and ventilation (HVAC) equipment, etc.

Smart appliance 130 is controlled by dynamic user program 122. In the various embodiments of the present invention, smart appliance 130 may represents an air conditioning unit, a heating unit, a ventilation system, cooking equipment or any other type of object associated with the IOT. Smart appliance 130 includes sensor(s) 132.

Sensor(s) 132 detect and/or measure various environmental aspects in or around smart appliance 130. Utilizing the IOT, sensor(s) 132 detects aspects of the physical world, and integrates such measurements into the electronic system. In an embodiment of the present invention, sensor(s) 132 may detect the ambient temperature of smart appliance 130, and transmit such information to dynamic user program 122. For example, if dynamic user program 122 determines that the temperature of a user's house needs be at a specific level in order to maintain the user's ideal physiological temperature, then through sensor(s) 132, dynamic user program 122 will know either to change (raise or lower the temperature) or maintain the current temperature of smart appliance 130.

Smart appliance 130 allows for automatic customization by dynamic user program 122. For example, smart appliance 130 may be controlled via a thermostatic control interface for an air conditioning or heating unit, wherein dynamic user program 122 can raise or lower the environmental temperature based on the user's determined geographical and/or physiological need. In another example, smart appliance 130 may be controlled via thermostatic control interface for an oven, wherein dynamic user program 122 can raise the oven temperature based on the user's determined geographical and/or physiological need.

In the various embodiments of the present invention, wearable device 140 represents wearable devices. For example, wearable device 140 might be smart watches, capable of detecting various inputs and transmitting data to server 120. Wearable device 140 may be multi-purpose devices that, for example, include a telephone, or digital music player, a fitness tracker, a ring, etc. Examples of wearable device 140 include, but are not limited to, a ring, a bracelet, a wristband or a wristwatch. Generally, wearable device 140 is wearable and able to detect various geographical and physiological aspects of the user. In an exemplary embodiment, wearable device 140 is a device worn by a user. Wearable device 140 includes sensors(s) 142.

Wearable device 140 may be provided in various form factors and may be designed to be worn in a variety of ways. In some embodiments of the present invention, a wearable device 140 is a smart watch. A smart watch is a computerized wristwatch with functionality that is enhanced beyond mere time keeping; rather a smart watch is essentially a wearable computer. Many smart watches can run applications, while others contain additional capabilities, for example, making and receiving phone calls, replacing a traditional smart phone. In other embodiments of the present invention, a wearable device 140 is a wrist band.

In an embodiment, wearable device may include a user interface (not show), allowing the user to override, if necessary, dynamic user program 122. A user interface may include a graphical user interface.

Sensor(s) 142 sense, detect and/or measure various movements and physiological conditions of a user. For example, sensor(s) 142 might detect motion of the user, via accelerometers, gyroscopes etc. Similarly, sensor(s) 142 may include access to a global positioning system (GPS) allowing dynamic user program 122 to determine the exact location and speed of travel of the user. Additionally, sensor(s) 142 may detect physiological aspects of the user such as body temperature, heart rate, blood pressure, and the like. Sensor(s) 142 may be any sensor or sensor system known in the art to assist dynamic user program 122 in determining aspects of the user, in order ensure the health of the user.

One of ordinary skill in the art will appreciate that any arrangement of input sensors may be included on wearable device 140 to receive data of the user. Sensors 142 of wearable device 140 may include, but are not limited to, accelerometers, gyroscope, thermometer, altimeter, barometer, compass, location determining device (e.g., GPS), proximity sensors, motion detectors, touch sensors, or the like. As one skilled in the art may see, any sensor or sensor combination in wearable device 140 may be used without deviating from the invention, as sensor(s) 142 permit a user to interact with wearable device 140.

Wearable device 140 may include an information repository as well as additional components not shown.

In an embodiment, wearable device 140 may leverage other devices external to the wearable device such as a mobile phone or a personal computer. For example, wearable device 140 may access a user's smart TV to determine how much television the user watched and recommend low calorie food as the user may have been inactive for a period of time.

The concepts disclosed and discussed herein, may be applied to both, a standalone wearable device (similar to that of wearable device 140), as well as a wearable device that leverages functionalities provided in external devices, e.g., smartphones, wireless headphones, etc.

Figure 2A:
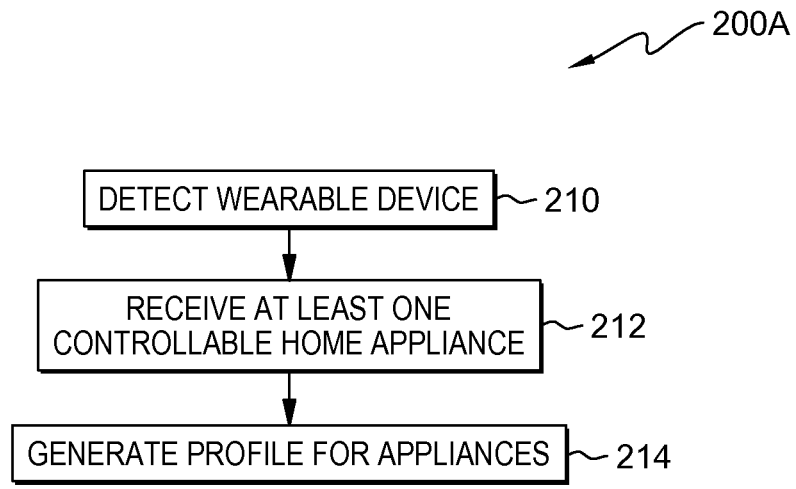
FIG. 2A is a flowchart illustrating the operational steps for coordinating appliance profiles, in accordance with an embodiment of the present invention.
Figure 2B:
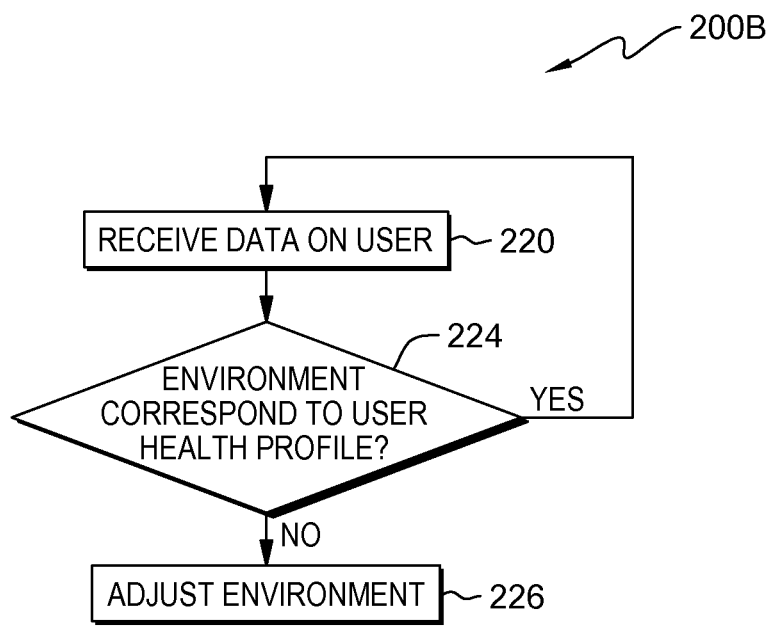
FIG. 2B is a flowchart illustrating operational steps for controlling a user's environment, in accordance with an embodiment of the present invention.

Reference is now made to FIG. 2A and FIG. 2B. FIG. 2A is flowchart 200A illustrating operational steps for coordinating appliance profiles, in accordance with an embodiment of the present invention. FIG. 2B is flowchart 200B illustrating operational steps for controlling a user's environment, in accordance with an embodiment of the present invention.

Flowchart 200A depicts dynamic user program 122 acquisition of information and determining an appropriate user profile. In step 210, dynamic user program 122, detects a wearable device, similar to that of wearable device 140, of FIG. 1. In an embodiment, a wearable device may be capable of detecting various user parameters such as one's physical conditions. Similarly, in an embodiment, the detected wearable device may detect and/or determine a user's activity level. For example, the detected wearable device providing physiological conditions on the user may provide details such as, the sleep the user had, the kind of working the user had completed, the type of workout completed, users current body temperature and the like. In an embodiment wearable device may sense the user's surroundings, such as temperature, barometric pressure, humidity level etc. An embodiment of the present invention may also notate the time of each sensor reading.

Wearable device 140 may keep track of the user's physiological conditions. Alternatively, an information repository associated with wearable device or dynamic user program 122 may keep track of the user's physiological conditions. A user's physiological conditions may include workout duration, workout intensity, calorie count, sleep duration, body temperate, daily routine, etc.

In step 212 dynamic user program 122 receives at least one controllable smart appliance, similarly to that of smart appliance 130 of FIG. 1. In an embodiment, smart appliance 130 has an ability to communicate with dynamic user program 122. In an embodiment, smart appliance 130 may be registered and/or controlled by dynamic user program 122. In an embodiment smart appliance 130 may be controlled directly from wearable device 140.

Optionally in step 212, dynamic user program 122 may receive a health profile of a user. In an embodiment, dynamic user program 122 may receive a health profile as created by a user's doctor, dietitian, family member, or any other individual who has knowledge of the user and can assist the user in creating a health profile. Alternatively, or additionally, dynamic user program 122 may generate the health profile of the user by prompting the user with multiple questions and physiological readings in order to create a baseline of the user.

In step 214, dynamic user program 122, generates a profile for the appliances based on the user's health profile (as received in step 220). In an embodiment, dynamic user program 122, may utilize various readings from smart appliance 130 and will determine IOT appliance settings that comply with the health profile of the user. Based on the generated profile of appliances, dynamic user program 122, may, based on the immediate health needs of the user, automatically alter the smart appliances.

Flowchart 200B depicts dynamic user program 122 acquiring of information from sensors and determining an appropriate environment for the user. In step 210, dynamic user program 122, receives information from a user's wearable device 140 and/or from a smart appliance 130 registered to a user's wearable device 140. Received information may relate to any physiological condition of the user as sensed by a sensor 142 on wearable device 140.

In step 224, dynamic user program 122, analyzes the data and demines whether the environment corresponds to the user health profile as generated in step 214. Based on the physiological conditions and the respective attributes obtained by wearable device 140 for a user, dynamic user program 122, manages all the registered consumer smart devices and automatically adjusts each device to be best suited for the user. If in step 224 it is determined that the environment is within the parameters set within the user health profile, then dynamic user program 122, returns to step 220 waiting to receive new data on the user.

However, if the environment does not correspond to the user health profile, then in step 226, dynamic user program 122 adjusts the environment by controlling one or more smart devices. Dynamic user program 122 achieves automatic customization of the user's appliances as the program dynamically adapts following the user's physiological attributes obtained from the user's wearable device. In an embodiment, dynamic user program 122, ensures no adverse impact on the user's health. In an embodiment, dynamic user program 122, optimizes the usage of the consumer appliances, as they are utilized only when necessary as they adapt specifically to the user.

In an embodiment, based on the received readings in step 220, dynamic user program 122 will inform the smart appliances about the required settings that comply with the user health profile of the user. Thereby the smart appliance will adjust to meet the health needs of the user.

Figure 3:
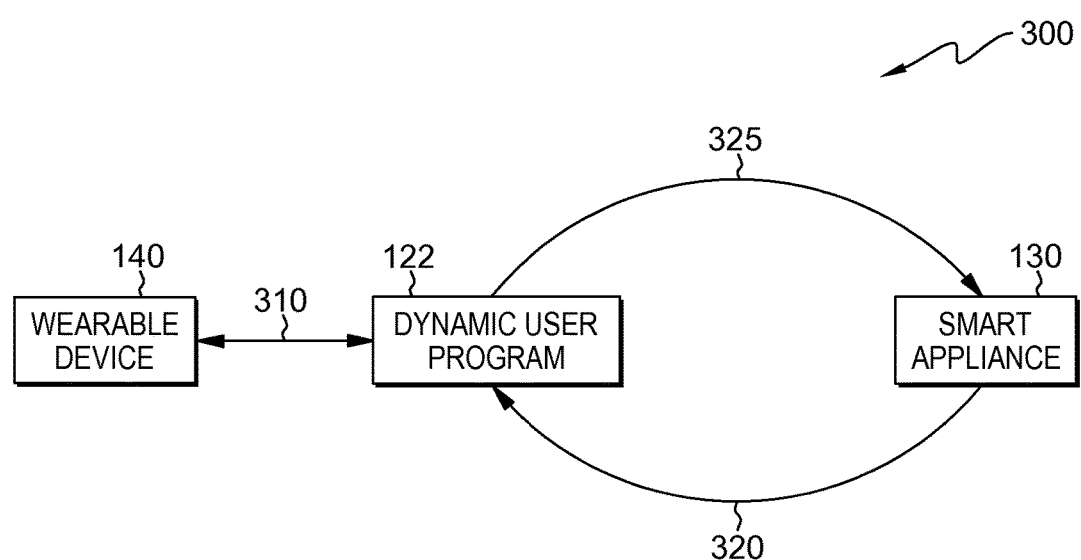
FIG. 3 is a block diagram depicting communication between components of FIG. 1, in accordance with an embodiment of the present invention.

Reference is now made to FIG. 3. FIG. 3 is a block diagram depicting communication between components of FIG. 1, in accordance with an embodiment of the present invention. Embodiment 300 portrays the communication between three components, wearable device 140, dynamic user program 122, and smart appliance 130. It is noted that embodiment 300 may contain additional components not shown, for example, there can be more than one smart appliance.

Line 310 represents wearable device 140's continuous monitor of a user's physiological attributes. Line 310 also represents syncing and communicating the user's physiological attributes to dynamic user program 122.

Line 320 represents the syncing of smart appliances 130 current state to dynamic user program 122. Smart appliance 130 sends current environmental status updates to dynamic user program 122. In return for a status update coupled with the user's physiological condition, line, 325 represents dynamic user program 122 automatic customization of smart appliances 130, based on wearable data.

In an exemplary embodiment, dynamic user program 122 oversees and prevents health issues if a user's schedule changes. For instance, if an individual is in a hot environment, and suddenly switches to a cold environment, then the individual may face health issues such as, an asthma attack or dry skin. For example, dynamic user program 122 detects, from wearable device 140, that the user is working out and in a warm environment and dynamic user program 122 detects, from the user's smart air conditioning appliance, that the user's house is set to cool; then dynamic user program 122 may override the preset temperature of the smart air conditioning unit and fine tune the actual temperature to meet the physiological needs of the user. Further, if dynamic user program 122 determines the user is 20 minutes away from the house and it takes 13 minutes to bring the temperature of the house to the ideal setting, then dynamic user program 122, may engage the air conditioning 7 minutes after the determination, to most effectively and efficiently use electricity in conjunction to benefiting the user's health.

Similarly, dynamic user program 122, may even preset the user's water temperature in the shower to align with the user's physiological conditions, in particular the user's body temperature.

In an exemplary embodiment, dynamic user program 122, may override a predefined smart appliance schedule due to a change in the user's schedule. For example, if the user has a daily routine of waking up in the morning, placing a high caloric dinner in the microwave oven to eat after work, going to the gym, then work, then on his way home from work at a certain predefined distance, the microwave oven automatically turns on, cooking his meal so it is ready when the user arrives at home following his day at work. However, if the user's routine changed as the user skipped the gym, then the user would need to alter the predefined program set for the microwave oven, as the food may not be recommended if the user did not work out. Therefore, dynamic user program 122 detects, from wearable device 140, that the user did not work out today, breaking from the normal pattern. Therefore, dynamic user program 122 determines that the user should not eat a high caloric dinner, and will interrupt the predefined program for the microwave oven.

In this exemplary embodiment, dynamic user program 122, may assist the user in determining what to eat based on current physiological conditions. For example, if a dietitian provided the user with a diet App to help the user order food, dynamic user program 122 may recommend specific food based on whether the user received less sleep, partook in an unplanned activity, or exhibited measurable signs of stress.

Figure 4:
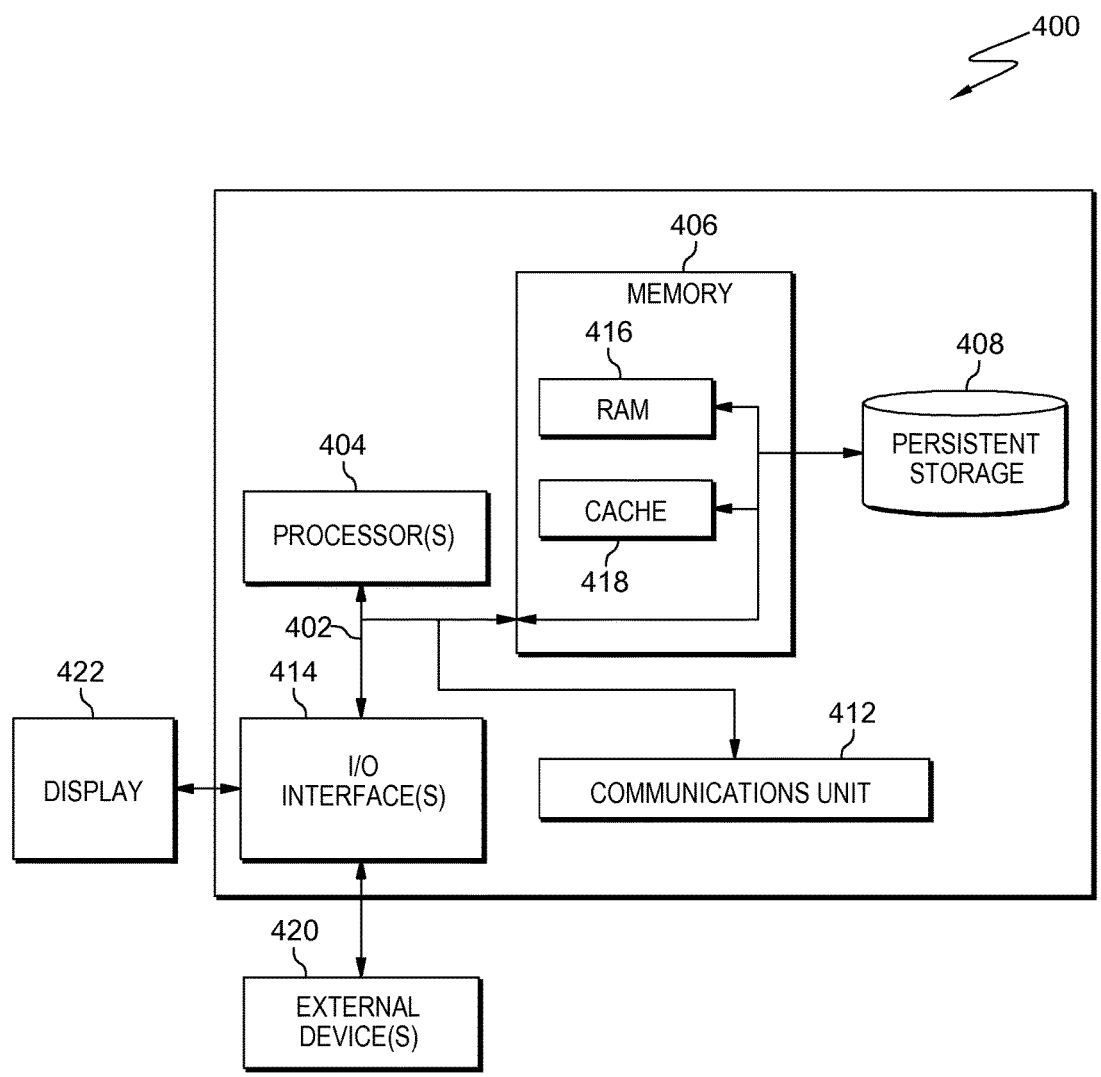
FIG. 4 is a block diagram of the internal and external components of a computer system, in accordance with an embodiment of the present invention.

FIG. 4 is a block diagram of internal and external components of a computer system 400, which is representative of the computer systems of FIG. 1, in accordance with an embodiment of the present invention. It should be appreciated that FIG. 4 provides only an illustration of one implementation, and does not imply any limitations with regard to the environments in which different embodiments may be implemented. Many modifications to the depicted environment may be made.

Computer system 400 includes communications fabric 402, which provides communications between computer processor(s) 404, memory 406, persistent storage 408, communications unit 412, and input/output (I/O) interface(s) 414. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer readable storage media. In this embodiment, memory 406 includes random access memory (RAM) 416 and cache memory 418. In general, memory 406 can include any suitable volatile or non-volatile computer readable storage media.

Persistent storage 408 may include, for example, a plurality of magnetic hard disk drives. Programs are stored in persistent storage 408 for execution and/or access by one or more of the respective computer processors 404 via one or more memories of memory 406. In this embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 412, in these examples, provides for communications with other data processing systems or devices. In these examples, communications unit 412 includes one or more network interface cards. Communications unit 412 may provide communications through the use of either or both physical and wireless communications links. Software and data used to practice embodiments of the present invention can be downloaded to computer system 400 through communications unit 412 (i.e., via the Internet, a local area network, or other wide area network). From communications unit 412, the software and data may be loaded to persistent storage 408.

I/O interface(s) 414 allows for input and output of data with other devices that may be connected to computer system 400. For example, I/O interface 414 may provide a connection to external devices 420, such as a keyboard, keypad, a touch screen, and/or some other suitable input device. External devices 420 can also include portable computer readable storage media such as, for example, thumb drives, portable optical or magnetic disks, and memory cards. Software and data used to practice embodiments of the present invention, can be stored on such portable computer readable storage media and can be loaded onto persistent storage 408 via I/O interface(s) 414. I/O interface(s) 414 also connect to a display 422.

Display 422 provides a mechanism to display data to a user and may be, for example, a computer monitor. Display 422 can also be an incorporated display and may function as a touch screen, such as a built-in display of a tablet computer.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:

identifying, by one or more processors, a wearable device, with at least one user sensor, wherein the wearable device is associated with a user, and wherein the at least one user sensor monitors at least one physiological aspect of the user;

identifying, by one or more processors, at least one controllable appliance associated with the user, with at least one appliance sensor and at least one controllable setting;

receiving, by one or more processors, health information of the user from the identified wearable device, wherein the health information includes data associated with the at least one physiological aspect of the user;

in response to receiving the health information of the user, generating, by one or more processors, a user profile, wherein the user profile comprises parameters related to the health of the user;

receiving, by one or more processors, a first set of data from the wearable device and a second set of data from the at least one controllable appliance;

determining, by one or more processors, whether the received first set of data and the received second set of data matches the parameters related to the health of the user; and in response to determining that the received data does not match the parameters related to the health of the user, adjusting, by one or more processors, at least one controllable setting of the at least one controllable appliance, so that the second set of data from the at least one controllable appliance and the first set of data from the wearable device matches the user profile.

2. The method of claim 1, wherein the at least one physiological aspect comprises at least one of the following:

data relating to activity of the user;

data relating to sleep of the user; and data relating to food consumption of the user.

3. The method of claim 1, wherein the at least one controllable setting of the at least one controllable appliance comprises at least one of the following:
   a temperature control;
   a power setting control; and
   an overriding control for a predefined setting.

4. The method of claim 1, wherein the parameters relating to the health of the user comprise:
   an ambient temperature range for the user; and
   food recommendation for the user.

5. The method of claim 1, further comprising:
   providing a user interface associated with the at least one controllable appliance, wherein the user interface allows a user to adjust the parameters relating to the user profile.

6. The method of claim 1, wherein generating a user profile comprises:
   analyzing, by one or more processors, a set of parameters wherein the set of parameters are based, at least in part, on the health profile of the user, and a schedule of the user.

7. A computer program product comprising:
   a computer readable storage medium and program instructions stored on the computer readable storage medium, the program instructions comprising:
   program instructions to identify a wearable device, with at least one user sensor, wherein the wearable device is associated with a user, and wherein the at least one user sensor monitors at least one physiological aspect of the user;
   program instructions to identify at least one controllable appliance associated with the user, with at least one appliance sensor and at least one controllable setting;
   program instructions to receive health information of the user from the identified wearable device, wherein the health information includes data associated with the at least one physiological aspect of the user;
   in response to receiving the health information of the user, program instructions to generate a user profile, wherein the user profile comprises parameters related to the health of the user;
   program instructions to receive a first set of data from the wearable device and a second set of data from the at least one controllable appliance;
   program instructions to determine whether the received first set of data and the received second set of data matches the parameters related to the health of the user; and
   in response to determining that the received data does not match the parameters related to the health of the user, program instructions to adjust at least one controllable setting of the at least one controllable appliance, so that the second set of data from the at least one controllable appliance and the first set of data from the wearable device matches the user profile.

8. The computer program product of claim 7, wherein the at least one physiological aspect comprises at least one of the following:
   data relating to activity of the user;
   data relating to sleep of the user; and
   data relating to food consumption of the user.

9. The computer program product of claim 7, wherein the at least one controllable setting of the at least one controllable appliance comprises at least one of the following:
   a temperature control;
   a power setting control; and
   an overriding control for a predefined setting.

10. The computer program product of claim 7, wherein the parameters relating to the health of the user comprise:
    an ambient temperature range for the user; and
    food recommendation for the user.

11. The computer program product of claim 7, further comprising:
    program instructions to provide a user interface associated with the at least one controllable appliance, wherein the user interface allows a user to adjust the parameters relating to the user profile.

12. The computer program product of claim 7, wherein program instructions to generate a user profile comprises:
    program instructions to analyze a set of parameters wherein the set of parameters are based, at least in part, on the health profile of the user, and a schedule of the user.

13. A computer system comprising:
    one or more computer processors;
    one or more computer readable storage media;
    program instructions stored on the one or more computer readable storage media for execution by at least one of the one or more processors, the program instructions comprising:
    program instructions to identify a wearable device, with at least one user sensor, wherein the wearable device is associated with a user, and wherein the at least one user sensor monitors at least one physiological aspect of the user;
    program instructions to identify at least one controllable appliance associated with the user, with at least one appliance sensor and at least one controllable setting;
    program instructions to receive health information of the user from the identified wearable device, wherein the health information includes data associated with the at least one physiological aspect of the user;
    in response to receiving the health information of the user, program instructions to generate a user profile, wherein the user profile comprises parameters related to the health of the user;
    program instructions to receive a first set of data from the wearable device and a second set of data from the at least one controllable appliance;
    program instructions to determine whether the received first set of data and the received second set of data matches the parameters related to the health of the user; and
    in response to determining that the received data does not match the parameters related to the health of the user, program instructions to adjust at least one controllable setting of the at least one controllable appliance, so that the second set of data from the at least one controllable appliance and the first set of data from the wearable device matches the user profile.

14. The computer system of claim 13, wherein the at least one physiological aspect comprises at least one of the following:
    data relating to activity of the user;
    data relating to sleep of the user; and
    data relating to food consumption of the user.

15. The computer system of claim 13, wherein the at least one controllable setting of the at least one controllable appliance comprises at least one of the following:
    a temperature control;
    a power setting control; and
    an overriding control for a predefined setting.

16. The computer system of claim 13, wherein the parameters relating to the health of the user comprise:
- an ambient temperature range for the user; and
- food recommendation for the user.

17. The computer system of claim 13, wherein program instructions to generate a user profile comprises:
- program instructions to analyze a set of parameters wherein the set of parameters are based, at least in part, on the health profile of the user, and a schedule of the user.

* * * * *